United States Patent
Berutti et al.

(10) Patent No.: US 7,435,086 B2
(45) Date of Patent: Oct. 14, 2008

(54) ENDODONTIC TOOL HAVING REDUCED TORQUE DEMANDS

(76) Inventors: Elio Vincenzo Giovanni Berutti, Via Servais 140-17, Torino (IT) 10146; Arnaldo Castellucci, Via Palestro, 3, Florence (IT) 50123; Giuseppe Cantatore, 62, Via Della Luce, Roma (IT) 00153

( * ) Notice: Subject to any disclaimer, the term of this patent is extended or adjusted under 35 U.S.C. 154(b) by 234 days.

(21) Appl. No.: 11/195,101

(22) Filed: Aug. 2, 2005

(65) Prior Publication Data
US 2007/0031784 A1 Feb. 8, 2007

(51) Int. Cl.
*A61C 5/02* (2006.01)
(52) U.S. Cl. ..................................... 433/102
(58) Field of Classification Search ............... 433/102, 433/165
See application file for complete search history.

(56) References Cited

U.S. PATENT DOCUMENTS

| | | | |
|---|---|---|---|
| 4,443,193 A | 4/1984 | Roane | |
| 4,536,159 A | 8/1985 | Roane | |
| 4,934,934 A | 6/1990 | Arpaio, Jr. et al. | |
| RE34,439 E | 11/1993 | Heath | |
| 5,380,200 A | 1/1995 | Heath et al. | |
| 5,464,362 A | 11/1995 | Heath et al. | |
| 5,658,145 A | 8/1997 | Maillefer et al. | |
| 5,692,902 A | 12/1997 | Aeby | |
| 5,762,497 A * | 6/1998 | Heath | 433/102 |
| 5,873,719 A | 2/1999 | Calas et al. | |
| 5,897,316 A | 4/1999 | Buchanan | |
| 5,921,775 A | 7/1999 | Buchanan | |
| 5,975,899 A | 11/1999 | Badoz et al. | |
| 6,012,921 A | 1/2000 | Riitano | |
| 6,074,209 A | 6/2000 | Johnson | |
| 6,217,335 B1 | 4/2001 | Riitano et al. | |
| 6,267,592 B1 | 7/2001 | Mays | |
| 6,312,261 B1 | 11/2001 | Mays | |
| 6,315,558 B1 | 11/2001 | Farzin-Nia et al. | |
| 6,390,819 B2 | 5/2002 | Riitano | |
| 6,419,488 B1 | 7/2002 | McSpadden et al. | |
| 6,514,076 B1 | 2/2003 | Bleiweiss et al. | |
| 6,520,774 B1 | 2/2003 | Mays | |
| 6,644,972 B1 | 11/2003 | Mays | |

(Continued)

FOREIGN PATENT DOCUMENTS

WO WO 97/21392 A1 6/1997
WO WO 2005/122941 A1 12/2005

OTHER PUBLICATIONS

Search Report, date Nov. 14, 2006, European Patent.

*Primary Examiner*—John J Wilson
(74) *Attorney, Agent, or Firm*—Gable Gotwals

(57) ABSTRACT

A dental reamer/file is in the form of an elongated shank having a proximal end portion and a distal end and a tapered working portion of determined length extending therebetween, the external surface of the shank working portion having at least two equally spaced apart continuous concave helical flutes and therebetween an equal number of spiraled, spaced apart flanges, each flange having in a plane perpendicular to the length of a longitudinal axis of the shaft an outer end defined by a first and a second surface intersecting at a point of maximum radius from the axis, the first surface being relatively short and the second surface relatively longer, the point of maximum radius providing a spiraled scraping edge.

15 Claims, 1 Drawing Sheet

U.S. PATENT DOCUMENTS

| | | |
|---|---|---|
| 6,746,245 B2 | 6/2004 | Riitano et al. |
| 2002/0119418 A1* | 8/2002 | Matsutani et al. ........... 433/102 |
| 2003/0077553 A1 | 4/2003 | Brock |
| 2004/0023186 A1 | 2/2004 | McSpadden |
| 2004/0043357 A1 | 3/2004 | Garman |
| 2004/0058297 A1 | 3/2004 | Danger |
| 2004/0121283 A1 | 6/2004 | Mason |
| 2005/0272004 A1* | 12/2005 | Desrosiers .................. 433/102 |
| 2005/0282108 A1* | 12/2005 | Goodis ....................... 433/102 |
| 2006/0246394 A1* | 11/2006 | Cantatore et al. ........... 433/102 |

\* cited by examiner

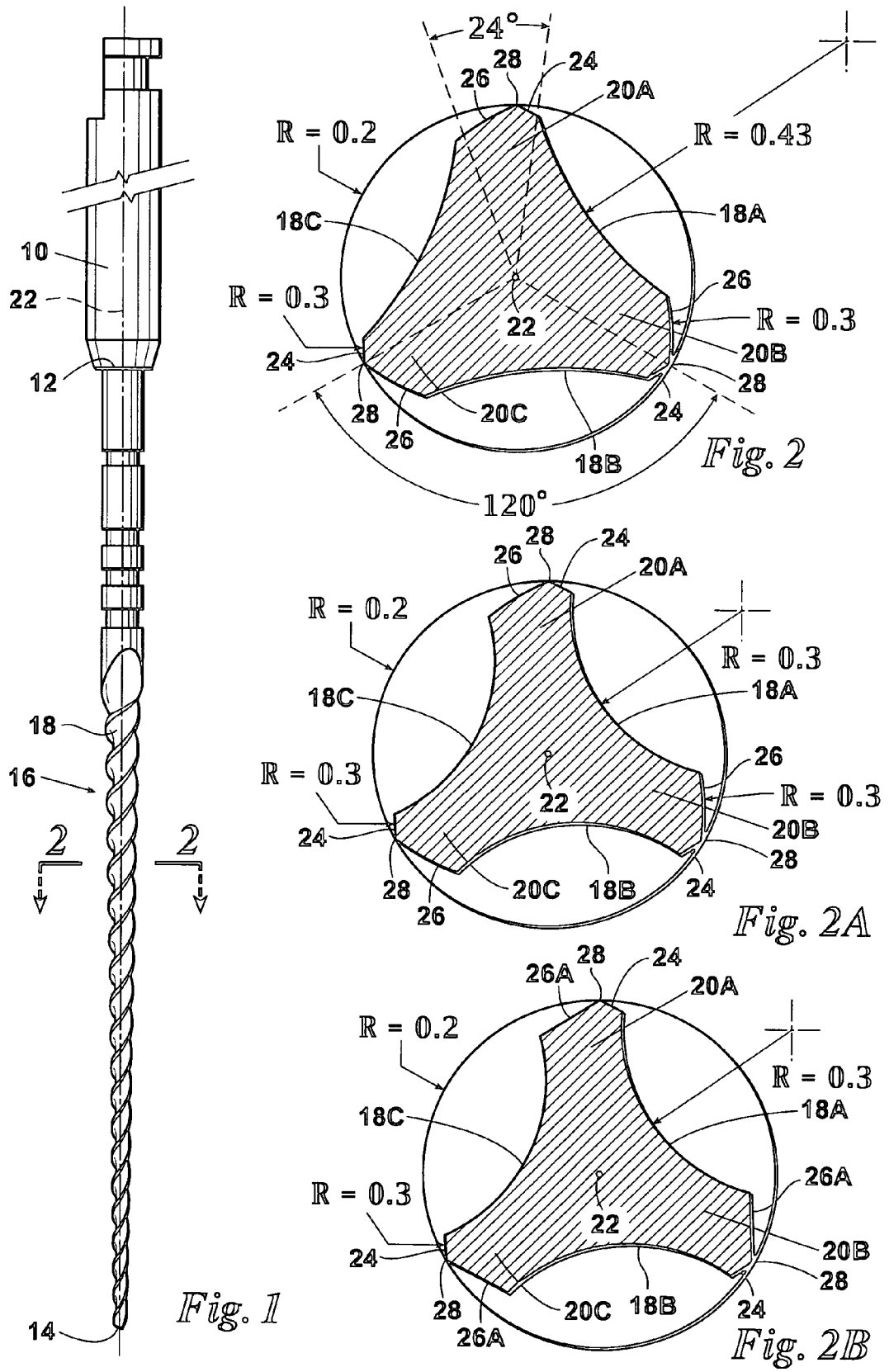

ENDODONTIC TOOL HAVING REDUCED TORQUE DEMANDS

REFERENCE TO PENDING APPLICATIONS

This application is not related to any pending domestic or international patent applications.

REFERENCE TO MICROFICHE APPENDIX

This application is not referenced in any microfiche appendix.

BACKGROUND OF THE INVENTION

1. Field of the Invention

This invention relates to a flexible tool that is particularly adaptable for use as an endodontic instrument, most particularly, an endodontic reamer/file for use by practitioners in removing the pulpal material from an exposed root of a tooth and for shaping the root canal to receive filler material therein.

2. Background of the Invention

One of the most significant advancements in dentistry in recent years has been improved treatment of abscessed teeth. In the past a tooth, once abscessed, was usually pulled as the only remedy for alleviating the intense pain. By "abscessed" usually means that the root canal of the tooth becomes infected and the infection causes pressure on the tooth and the nerve endings associated therewith that result in, sometimes, almost unbearable pain. With the advent of endodontics the drastic measure of extracting a tooth that has become abscessed has been eliminated.

The first step in the endodontic treatment of an abscessed tooth is to drill an opening in the crown of the tooth to provide access to the root canal. Once the root canal is exposed, the practitioner then must thoroughly clean the root canal of pulpal material since if the pulpal material is not thoroughly and carefully removed it can be the source of continued infection. Not only is it necessary that the pulpal material be removed but the root canal usually must be shaped in such a way as to permit filling of the root canal with a filler material. While other types of filler materials have been provided still at the present time the most common filler is a paste-like material referred to as "gutta-percha." If the canal is not properly cleaned and shaped the step of filling with gutta-percha, or other filler material, may leave void areas that invite the introduction into the root canal of organic matter that can be followed by bacterial action. For these reasons much of the effort of a practitioner to successfully accomplish the endodontic treatment of an abscessed tooth is the cleaning and shaping of the root canal. These steps are accomplished utilizing small diameter tapered reamer/files that are inserted by the practitioner through the exposed crown area into the root canal. The canal must be cleaned from the crownal area advancing to the root apex.

A root canal is typically in a tapered configuration, that is, the cross-sectional area of canals is usually greater near the crown of the tooth and is at a minimum at the apex of the tooth, that is, the distal end of the root canal. While the root canal is naturally tapered it is not tapered symmetrically and the canal can have inclusions in intermediate portions between the apex and the crown area that interfere with the passage of filler material. Therefore the root canal must be shaped to remove unnecessary intrusions and to improve the chances that the practitioner can successfully fill the root canal.

Files are usually provided with a small cylindrical plastic handle portion by which the practitioner manually manipulates the files. By "manipulation" means inserting a file into a canal and reciprocating it to file away intrusions and at the same time to remove pulpal material. Typically the practitioner inserts a file to the point of resistance and then rotates and reciprocates the file to engage spiral scraping edges with the canal wall. The file is then extracted to remove pulpal material and matter scraped from the wall. This procedure is repeated as necessary to clean the entire length of the canal. In the cleaning process the practitioner usually starts with a file of a small diameter and then, as progress is made in cleaning and shaping the canal, larger diameter files are employed until the root canal is shaped and cleaned to the apex. Accordingly, endodontic files usually come in sets of standard tapers and varying from smaller to larger diameters.

Instead of manually rotating an endodontic file the practitioner may insert the file proximal end into the chuck of a hand piece by which the file is mechanically rotated and manipulated.

Root canals are characteristically not straight. Some root canals curve more than others but few are perfectly straight from the crown to the apex. Therefore it is important that files be flexible so as to be able to follow the natural curvature of the root canal as it is cleaned and shaped from the tooth crown to the tooth apex. If a file is too stiff it can result in the file protruding through a side wall of a tooth root which can introduce an avenue of infection into the tooth. Further, if the file is stiff it is less successful in cleaning the entire area of a canal since the stiffness will cause the file to be deflected drastically to one side of a curve in a canal leaving a portion of the wall that defines the curve unexposed to the action of the file. Therefore, a high degree of flexibility is a desirable characteristic of an endodontic file.

In addition, the strength of a file is very important. In the process of reciprocating and rotating a file in a tooth it is possible for the file to break, leaving a broken part in the tooth. This creates a serious problem for the practitioner. Accordingly, it has long been a desire of the dental profession to have available dental files that are highly flexible and yet have strong torsional strengths to resist breakage as a result of the twisting and pulling actions as a file is manipulated within a root canal. The present invention provides a way of substantially decreasing the torque demand of dental files.

The introduction of nickel-titanium alloy for use in manufacturing endodontic instruments has greatly simplified root canal shaping procedures. Due to greater flexibility nickel-titanium has been found to be better than stainless steel in maintaining the original shape of files. Moreover, these instruments are also characterized by a larger maximum torque to failure than stainless instruments.

The nickel-titanium mechanically driven engine instrument operates turning continuously in a clock or counter-clockwise direction. At the same time it is alternatively inserted and extracted from the root canals. The first working condition leads to the presence of a constant tangential stress whose maximum value depends on the canal anatomy and dentin hardness. In the second working condition, the instrument is constrained to follow the geometry of the root canals and is subjected to a normal stress that depends on the instrument cross section dimension and shape.

Normal stresses are responsible of the low cycle fatigue failure of instruments. The maximum tangential and normal stresses together are responsible for the ductile failure of instruments. The optimal design of an instrument cross section is extremely important because it directly influences its torsional and bending properties and, consequently, the maximum normal and tangential stress values.

3. Description of the Prior Art

For background information relating to the subject matter of this invention and specifically relating to dental reamer/files, reference may be had to the following issued United States patents and publications:

tapered working portion that extends from the proximal portion to the distal end. The shank also includes either an enlarged diameter handle portion, typically made of plastic for manually manipulating the file or a smaller diameter metal portion, usually integral with the file, that is configured to be received in a dental hand piece by which the file is mechanically rotated and can be manipulated by the practitioner.

| PATENT NUMBER | INVENTOR(S) | ISSUE DATE | TITLE |
| --- | --- | --- | --- |
| 4,443,193 | Roane | Apr. 17, 1984 | Endodontic Instrument |
| 4,536,159 | Roane | Aug. 20, 1985 | Endodontic Instrument |
| 4,934,934 | Arpaio, Jr. et al. | Jun. 19, 1990 | Dental File/Reamer Instrument |
| 5,380,200 | Heath et al. | Jan. 10, 1995 | Endodontic Instrument Of Predetermined Flexibility |
| 5,464,362 | Heath et al. | Nov. 7, 1995 | Endodontic Instrument |
| 5,658,145 | Maillefer et al. | Aug. 19, 1997 | Set Of Instruments For Boring Dental Radicular Canals And Method Therefor |
| 5,692,902 | Aeby | Dec. 2, 1997 | Set Of Instruments For The Boring Of Radicular Dental Canals |
| 5,873,719 | Calas et al. | Feb. 23, 1999 | Dental Reamer |
| 5,897,316 | Buchanan | Apr. 27, 1999 | Endodontic Treatment System |
| 5,921,775 | Buchanan | Jul. 13, 1999 | Endodontic Treatment System |
| 5,975,899 | Badoz et al. | Nov. 2, 1999 | Dental Reamer |
| 6,012,921 | Riitano | Jan. 11, 2000 | Endodontic Systems For The Anatomical, Sectional And Progressive Corono-Apical Preparation Of Root Canals With Three Sets Of Dedicated Instruments |
| 6,074,209 | Johnson | Jun. 13, 2000 | Reduced Torque Endodontic File |
| 6,217,335 | Riitano et al. | Apr. 17, 2001 | Endodontic Systems And Methods For The Anatomicall, Sectional And Progressive Corono-Apical Preparation Of Root Canals With Minimal Apical Intrusion |
| 6,267,592 | Mays | Jul. 31, 2001 | Highly Flexible Instrument For Dental Applications |
| 6,312,261 | Mays | Nov. 6, 2001 | Endodontic Obturator With Removable Carrier And Method Of Use Thereof |
| 6,315,558 | Farzin-Nia et al. | Nov. 13, 2001 | Method Of Manufacturing Superelastic Endodontic Files And Files Made Therefrom |
| 6,390,819 | Riitano | May 21, 2002 | Endodontic Systems And Methods For The Anatomical, Sectional And Progressive Corono-Apical Preparation Of Root Canals With Dedicated Stainless Steel Instruments And Dedicated Nickel/Titanium Instruments |
| 6,419,488 | McSpadden et al. | Jul. 16, 2002 | Endodontic Instrument Having A Chisel Tip |
| 6,514,076 | Bleiweiss et al. | Feb. 4, 2003 | Precipitation Hardenable Stainless Steel Endodontic Instruments And Methods For Manufacturing And Using The Instruments |
| 6,520,774 | Mays | Feb. 18, 2003 | Highly Flexible Instrument For Medical Applications |
| 6,644,972 | Mays | Nov. 11, 2003 | Endodontic Obturator With Removable Carrier And Method Of Use Thereof |
| 6,746,245 | Riitano et al. | Jun. 8, 2004 | Methods For Cleaning And Shaping Asymmetrical Root Canals In An Anatomical Fashion |
| 2004/0121283 | Mason | Jun. 24, 2004 | Precision Cast Dental Instrument |
| 2003/0077553 | Brock | Apr. 24, 2003 | Endodontic Instrument Having Notched Cutting Surfaces |
| 2004/0058297 | Danger | Mar. 2, 2004 | Root Canal Instrument |
| 2004/0043357 | Garman | Mar. 4, 2004 | Endodontic Instrument |
| 2004/0023186 | McSpadden | Feb. 5, 2004 | Multi-Tapered Endodontic File |
| Re. 34,439 | Heath | Nov. 9, 1993 | Dental Compactor Instrument |

BRIEF SUMMARY OF THE INVENTION

The invention herein is a dental reamer/file that is for use in performing endodontic procedures, that is, specifically, cleaning and shaping the root canal of a tooth to prepare the tooth to receive filler material, such as gutta percha.

The invention is specifically a file which may be manipulated manually or by machine, that is, a hand piece that is commonly used by endodontic practitioners. The file includes an elongated shank with a proximal end, a distal end and a The dental reamer/file of this invention includes an elongated shank having a proximal portion, a distal end and a tapered working portion extending from the proximal portion to the distal end. The external surface of the shank working portion is defined in part by a plurality of at least two equally spaced apart continuous concave helical flutes formed into a central core portion of the shank working portion. The flutes have therebetween an equal number of spiraled, spaced apart, flanges. Each flange has, in a plane perpendicular to the length of a longitudinal axis of the shaft, an outer end defined by a first and a second surface intersecting at a point of maximum radius from the axis. The first surface is relatively short and the second surface is relatively longer and convex arcuate. The point of maximum radius provides a scraping edge.

In a preferred embodiment, the first surface is a leading surface and the second surface is a trailing surface. However, when the file is rotated in the opposite direction, the leading surface becomes the trailing surface and vice versa. The shorter, first surface, can be substantially straight while the second, longer surface is preferably convex semi-circular. The flutes are preferably concave semi-circular and the depth of the flutes can vary to thereby vary the flexibility of the file. In a preferred arrangement the depth of the flutes vary along the length of the shank working portion.

A more complete understanding of the invention will be obtained from the following detailed description of the preferred embodiments and claims, taken in conjunction with the attached drawings.

BRIEF DESCRIPTION OF THE DRAWINGS

FIG. 1 is an elevational view of an endodontic file of the type that can be used to incorporate the principals of this invention. The file illustrated in FIG. 1 is the type for insertion into a hand piece so that the reamer/file is mechanically rotated and the axial advancement of the file into the root canal can be simultaneously varied by the practitioner.

FIG. 2 is a cross sectional view taken along the line 2-2 of FIG. 1. FIG. 2 shows the structure of the file working portion as being formed by three spiraled flutes providing three spiraled shank portions. That is, the shank portions are the areas between the flutes. While in the illustrated embodiment there are three flutes and correspondingly three flanges, the file of this invention may incorporate as few as two spaced apart spiral flutes separated by two spaced apart spiral flanges or can incorporate three, four or more spiraled flutes and flanges. In the preferred embodiment of the invention, the minimum number of spiraled flutes and flanges is two and the maximum number is four with either two or three flutes and flanges being preferred. The drawings of FIGS. 1 and 2 show the preferred arrangement including three flutes and three flanges.

FIG. 2A is a cross section view as in FIG. 2 but showing the arrangement wherein the depth of the flutes is greater. Specifically, FIG. 2A shows flutes that are semi-circular as does FIG. 2 however in FIG. 2A the radius of curvature of the flutes is reduced to thereby cause the flutes to be deeper. Since there is less cross-sectional area in the embodiment of FIG. 2A the reamer/file is correspondingly more flexible but at the same time has less torsional resistance.

FIG. 2B is a cross-sectional view as in FIG. 2A but showing an embodiment in which the first and second surfaces defining the outer end of each flange portion are both straight.

DETAILED DESCRIPTION OF THE PREFERRED EMBODIMENTS

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Shank portion |
| 12 | Proximal end |
| 14 | Distal end |
| 16 | Working portion |
| 18 | Helical flutes |
| 20 | Helical flanges |
| 22 | Longitudinal axis |
| 24 | First, short surface |
| 26 | Second, longer surface |
| 26A | Straight longer surface |
| 28 | Point of maximum radius, helical scraping edge |

Referring to the drawings and first to FIG. 1, an elevational view illustrates a typical endodontic file. The file includes a shank portion 10 that is configured to be received in the chuck of a hand tool by which the file is rotated and manipulated by an endodontic practitioner. In another common embodiment, not illustrated herein, instead of shank 10 a handle formed of a short length of generally cylindrical plastic material designed to be grasped between the thumb and forefinger of the practitioner by which the file is positioned and rotated can be employed. The file generally speaking is the same whether configured for mechanical rotation, that is, that includes shank 10 or instead, a manually manipulatible handle.

The shank portion 10 is at a proximal end 12 of the file. A distal end 14 is of substantially reduced diameter. Intermediate the proximal end 12 and distal end 14 is an elongated working portion generally indicated by the numeral 16. Formed on the exterior of the file working portion 16 is a plurality of at least two helical flutes 18. Each helical flute 18 is spirally formed on the exterior surface of the tool working portion 16. While a minimum of two spaced apart flutes may be employed, a preferred arrangement is to employ three such flutes that are illustrated flutes 18A, 18B and 18C in FIGS. 2 and 2A. While theoretically four or more flutes 18 can be employed, as a practical matter, the preferred arrangement is a minimum of two flutes and the preferred number is three as illustrated in FIGS. 2 and 2A.

Each flute 18 extends the length of the working portion 18 from adjacent the proximal end 12 to the distal end 14. The flutes 18 can vary in depth. In the preferred and illustrated arrangements, each of the flutes is semi-circular. FIGS. 2 and 2A illustrate two different length of radius of the semi-circular flutes. For instance, in FIG. 2, the flutes 18A, 188B and 18C each have a radius of curvature R equal to 0.43 inches, whereas in FIG. 2A, each of the flutes 18A, 18B and 18C is of a shorter radius, illustrated by example, as a radius of 0.3 inches. It must be kept in mind that FIGS. 2 and 2A are substantially enlarged compared to the typical endodontic file.

The flutes 18 are illustrated as being semi-circular, and this is a preferred arrangement, however it is not essential to the practice of the invention that flutes 18 be made exactly semi-circular. It is only important that the flutes have a concave surface. Further, whether semi-circular or some other concave configuration, the depth of the flutes can vary considerably. For instance, in one embodiment, a set of the endodontic files of this invention may be provided where the files are of different diameters but wherein the radius of the flutes is consistent from the proximal to the distal end of each file. Other sets of files may have an arrangement wherein the depth of the flutes 18 is related to the diameter of the file, that is, wherein larger diameter files have correspondingly greater relative depths of concavity, that is, reduced radiuses of curvature of the semi-circular flutes. In other sets of the files the concavity can vary along the length of each file. For instance, the file illustrated in FIG. 1 can be provided wherein the upper portion of the working portion 16, that is the portion most near the proximal end 12, can be semi-circular with a radius of curvature that is relative long while the flutes are of a reduced radius of curvature, such as shown in FIG. 2A, in the portion of the working surface of the file adjacent distal end 14. Generally speaking, the torsional resistance of each file is proportional to the depth of the concavity of flutes 18. That is, as the flutes are deeper in concavity, such as FIG. 2A compared to FIG. 2, the torsional resistance of the file decreases. Sets of files can be manufactured according to this invention in which the files in the set are characterized by high torque strength or resistance to cyclic fatigue Between each helical flute 18 is a spiraled, spaced apart, flange 20, designated as 20A, 20B and 20C. The flanges 20 are the portions of the file body that exists between flutes 18, and specifically between flutes 18A, 18B and 18C as seen in FIGS. 2 and 2A. In the illustrated embodiments since there are three helical flutes 18A, 18B and 18C there are three helical flanges 20A, 20B and 20C. Each of the flanges 20 has an outer end surface as seen in FIGS. 2 and 2A. The outer end surface of each flange 20 is defined by a first, relatively short surface 24 and a second relatively longer surface 26. The surfaces 24 and 26 of each flange meets at a point of maximum radius 28. Each point of maximum radius 28 provides a spiraled scraping edge. That is, the intersection of flange surfaces 24 and 26 provides for helical scraping edges 28 that extends the full length of the tool working portion 16.

Both the first, short surface 24 and the second, longer surface 26 of each flange 20 may be straight, however in the preferred arrangement each of the surfaces 24 and 26 are preferably arcuate. As an example, in FIG. 2 the first, short surface 24 of each flange portion has a radius of 0.3 inches as does each second, longer surface 26. The length of the radius of both the longer and shorter surfaces 24 and 26 can vary and it is not necessary that each have the same length radius.

The geometrical configuration of the endodontic file as illustrated in the cross-sectional views of FIGS. 2 and 2A define a file that is essentially a scraping rather than a cutting instrument. This is so since the point of maximum radius 28 is defined by surfaces that intersect at an included angle of greater than 90°. Either the short surfaces 24 or the longer surfaces 26 can be a leading surface. For instance, as seen in FIGS. 2 and 2A, if the file is rotated clockwise, then the short surfaces 24 become a leading surface and the longer surfaces 26 become a trailing surface. However, if the file is rotated in the counterclockwise direction, these conditions reverse.

First and second surfaces 24 and 26 of each flange portion in the illustrated arrangement are convex in the preferred arrangement. However, as previously indicated, instead of being convex the surfaces could be straight as illustrated in FIG. 2B. Specifically, in FIG. 2B both the first, short surface 24 and the second, longer surface 26B are straight. Further, it is noted that in the embodiment of FIG. 2A, the radius of curvature of each of the surfaces 24 and 26 is the same, that is, 0.3 inches which is greater than the radius of the file itself. As illustrated, the radius from the longitudinal axis 22 to each scraping edge 28 is 0.2 inches.

In the technology of manufacturing endodontic files there are two standard, well known and frequently employed cross-sectional arrangements. One is referred to as a ProFile arrangement and the other a ProTaper arrangement. The Pro-File cross sectional arrangement typically does not employ flutes but instead has convexed surfaces that interconnect to provide scraping edges. The ProTaper file employs flutes but the geometrical configuration of the outer surfaces that defines the outer working ends of each of the flanges typically consists of a single arcuatious surface, the arc having the same radius of curvature as the instrument point of maximum radius. The cross sectional embodiment of the invention herein as exemplified in FIGS. 2 and 2A takes advantage of the positive characteristics of both the ProFile and ProTaper files by avoiding the deficiency of these prior used designs. The ProTaper cross section is characterized by good cutting capabilities but by large moment of inertia (torsional stiffness), and a reduced capability of dentine debris removal. The ProFile cross section is characterized by a reduced moment of inertia, that is, it is a more compliant, torsional flexible instrument and has good capability of debris removal but has only a fair cutting capability. The ProTaper good cutting capabilities are obtained because of the helical concave flutes between the flanges whereas the presence of large groove between the flanges are responsibility for the ProFiles reduced moment of inertia and good capability of debris removal. The cross-sectional arrangement of FIGS. 2 and 2A keeps essentially the advantage of the ProFile edges by including concave helical flanges but introduces the presence of helical grooves between the helical flanges and in this way the cutting performance of the ProTaper file as well as the debris removal capability of the ProFile are essentially preserved. According to the principles of this invention dental tools can be dimensioned so that the cross-sectional torque strength to diameter ratio varies along the length of the tool shank from the proximal portion of the distal end. In another embodiment the dental tools can be dimensioned so that the torque strength of each file is determined by the concavity to diameter ratio of the helical flutes. In short, the invention herein preserves the best characteristics of known geometries used in the basic design of endodontic files.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An elongated dental tool for use in cleaning and/or shaping a tooth root canal comprising:

an elongated shank having a proximal end portion, a distal end and a tapered working portion of determined length extending from said proximal portion to said distal end;

the external surface of said shank working portion being defined in part by three substantially identical equally spaced apart continuous concave helical flutes formed into a central core portion of said shank working portion, said flutes having therebetween three substantially identical spiraled spaced apart flanges, each flange having in a plane perpendicular to the length of a longitudinal axis of said shank, a substantially identical outer end each defined by a first and a second surface intersecting at a point of maximum radius from said axis providing three spaced apart continuous symmetrical scraping edges that, in use, have contact with a tooth root canal, each scraping edge extending from said shank proximal end portion to said shank distal end, said first surfaces being relatively short and said second surfaces relatively longer, said first and second surfaces having a same radius of curvature in said plane, said radius of curvature being greater than a radius of said shank working portion, said first and second surfaces providing substantially similar scraping characteristics irrespective of the direction of rotation of the dental tool in a root canal, and thereby eliminating any cutting edges irrespective of the direction of rotation of the tool.

2. A dental tool according to claim 1 wherein each said flute is defined by a concave surface.

3. A dental tool according to claim 1 wherein said first surface is a leading surface in one direction of rotation of the instrument.

4. A dental tool according to claim 1 wherein said second surface is a leading surface in one direction of rotation of the instrument.

5. A dental tool according to claim 1 wherein said first surface is substantially straight.

6. A dental tool according to claim 1 wherein said first surface is convex arcuate.

7. A dental tool according to claim 1 wherein said second surface is convex arcuate.

8. A dental tool according to claim 1 wherein said concave helical flutes are, in a plane perpendicular said shaft longitudinal axis, semi-circular.

9. A dental tool according to claim 7 wherein the radius of curvature of said convex arcuate second surface is substantially equal to the radius of curvature of said concave helical flutes.

10. A dental tool according to claim 1 wherein said first and second surfaces are straight.

11. A dental tool according to claim 1 wherein both said first and second surface are convex arcuate.

12. A dental tool according to claim 1 wherein the cross-sectional torque strength to diameter ratio varies along the length of said shank working portion.

13. A dental tool according to claim 1 wherein said dental tool is one of a set of dental tools in which all the dental tools in said set are characterized by high torque strength.

14. A dental tool according to claim 13 wherein the torque strength of each dental tool in said set is determined by helical flute concavity to diameter ratios.

15. A dental tool according to claim 13 wherein said dental tool in one of a set of dental tools in which all dental tools in said set are configured for resistance to cyclic fatigue.

* * * * *